(12) United States Patent
Zappettini et al.

(10) Patent No.: US 11,428,662 B2
(45) Date of Patent: Aug. 30, 2022

(54) SENSOR, SYSTEM AND METHOD FOR MEASURING BIOCHEMICAL PARAMETERS IN THE SAP OF A PLANT

(71) Applicant: CONSIGLIO NAZIONALE DELLE RICERCHE, Rome (IT)

(72) Inventors: Andrea Zappettini, Reggio Emilia (IT); Nicola Coppedè, Parma (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 477 days.

(21) Appl. No.: 16/471,243

(22) PCT Filed: Dec. 19, 2017

(86) PCT No.: PCT/IB2017/058108
§ 371 (c)(1),
(2) Date: Jun. 19, 2019

(87) PCT Pub. No.: WO2018/116149
PCT Pub. Date: Jun. 28, 2018

(65) Prior Publication Data
US 2021/0132000 A1    May 6, 2021

(30) Foreign Application Priority Data
Dec. 23, 2016 (IT) ................. 102016000130803

(51) Int. Cl.
*G01N 27/414* (2006.01)
*G01N 27/327* (2006.01)
*G01N 27/333* (2006.01)
*G01N 33/00* (2006.01)

(52) U.S. Cl.
CPC ..... *G01N 27/4145* (2013.01); *G01N 27/3277* (2013.01); *G01N 27/3335* (2013.01); *G01N 33/0098* (2013.01)

(58) Field of Classification Search
None
See application file for complete search history.

(56) References Cited

U.S. PATENT DOCUMENTS 6,870,376 B1    3/2005  Gensler
2014/0093731 A1  4/2014  Bonfiglio et al.

OTHER PUBLICATIONS

V. Herrmann, et al. "In vivo pH measurement in xylem of broad-leaved trees using ion-sensitive field-effect transistors", Trees, 6(1), p. 13-18; March (Year: 1992).*
M. Demelas, "Chemo and biodetection in liquid with organic transistor", Ph.D. Dissertation, University of Cagliari, Italy, 2.1.5. Glucose Detection, p. 35-36 (Year: 2013).*
(Continued)

*Primary Examiner* — J. Christopher Ball
(74) *Attorney, Agent, or Firm* — Browdy and Neimark, P.L.L.C.

(57) ABSTRACT

An electrochemical sensor (10) for measuring biochemical parameters in the sap (L) of a plant (P), comprising: —a channel in which the sap (L) of a plant (P) flows; —a first electrically conductive filament (11) which crosses the channel; —a control electrode (12) which crosses the channel; wherein the channel comprises a conductor vessel (C) of a trunk (D) of the plant (P), and wherein the first filament (11) comprises a textile fiber (110) coated with a layer (111) of conductive polymer.

17 Claims, 2 Drawing Sheets

(56) References Cited

OTHER PUBLICATIONS

Battista Edmondo et al., "Enzymatic sensing with laccase-functionalized textile organic biosensors", Organic Electronics, pp. 51-57, vol. 40 (Oct. 2016).
Giuseppe Tarabella et al., "A single cotton fiber organic electrochemical transistor for liquid electrolyte saline sensing", Journal of Materials Chemistry, pp. 23830-23834, vol. 22, No. 45 (Jan. 2012).
Gibert D et al., "Sap flow and daily electric potential variations in a tree trunk", Plant Science, pp. 572-584, vol. 171, No. 5, (Nov. 2006).
E. Stavrinidou et al., "Electronic plants", Science Advances, pp. e1501136-e1501136, vol. 1., No. 10 (Nov. 2015).

* cited by examiner

SENSOR, SYSTEM AND METHOD FOR MEASURING BIOCHEMICAL PARAMETERS IN THE SAP OF A PLANT

TECHNICAL FIELD

The present invention relates to a sensor a system and the related method for measuring biochemical parameters in the sap of a plant.

PRIOR ART

Typically, to monitor the physiological properties of plants, metallic electrodes have been used, both to carry out electrical impedance measurements, and to realise potentiometric or amperometric electrochemical sensors. A first limit of known sensors is tied to the incompatibility and to the consequent rejection of the metallic electrodes by the plant in which they are inserted. The plant tends progressively to isolate the metallic electrodes and the cellular structure of the plant withdraws, forming a cavity around the metallic electrode, which little by little remains excluded from the plant.

A second limit of such sensors pertains to the possible types of measurements. With impedance measurements, no biochemical characterisations of the fluids of the plant are made, merely recording the variations in the impedance of the branch or of the trunk of the plant in which the electrodes are inserted. However, there is no direct information on the contents of specific analytes within the sap, which allow to understand the actual change of the plant.

Therefore, to make it possible and simple to carry out accurate electrochemical analyses, it is preferred to extract the sap from the plant for the execution of electrochemical potentiometric measurements on the extracted sap, but by so doing no continuous, real time monitoring of the monitored parameters is carried out, but rather sample-based monitoring.

A purpose of the present invention is to overcome the aforementioned drawbacks of the prior art, within a solution that is simple, rational and has low cost.

These purposes are achieved by the features of the invention set forth in the independent claim. The dependent claims outline preferred and/or particularly advantageous aspects of the invention.

DESCRIPTION OF THE INVENTION

The invention, specifically, provides an electrochemical sensor for measuring biochemical parameters in the sap of a plant, comprising:
a channel in which the sap of a plant flows;
a first electrically conductive filament which crosses the channel (in such a way as to be wet by the sap);
a control electrode (not in contact with the first filament) which crosses the channel (in such a way as to be wet by the sap);
wherein the channel comprises a conductor vessel (for example xylem and phloem) of a trunk of the plant, and wherein the first filament comprises a textile fiber coated with a layer of conductive polymer.

Thanks to this solution, the sensor is simple and not very invasive for the plant and, thanks to the biocompatibility properties of the functionalised fibres that constitute the first filament, it is possible to insert the sensor into the trunk of the plant without the rejection or exclusion of the sensor by the plant, even over long time intervals and allowing a natural absorption of the sap fluids of the plant by the textile fibre. In this way, the conductive textile fibre inserted in the plant allows a measurement of ionic concentration in the sap of the plant serving as an integrated biochemical sensor, where the active part is the structure of the plant, or the conductor vessels and the sap of the plant. In practice, by means of the biochemical sensor it is possible to conduct an analysis extending over time along the life of the plant, or carry out continuous real time monitoring of the composition of the sap of the plant, which is reflected on the life state of the plant itself and allows intervention to improve the nutritional level, the level of solar exposure, irrigation or other parameters of the plant as a function of the data measured by the sensor along the life of the plant.

Moreover, unlike known metallic electrodes, which allow to measure only electrical currents, thanks to the insertion of the textile fibre functionalised by a conductive polymer, the sensor is sensitive and directly measures the concentrations of positive ions (electrolytes) present in the sap in a minimally invasive manner, without compromising the physiology of the plant.

According to an aspect of the invention, moreover, the conductive polymer making up the layer can be chosen in the group among a poly(3,4-ethylenedioxythiophene)-based polymer (PEDOT), poly(pyrroles) (PPY), polycarbazoles, polyindoles, polyazepines, polyanilines (PANI), polyacetylenes (PAC), poly(p-phenylene vinylene) (PPV)), polymers added with micro or nano conductive particles, such as silver or gold, carbon nanotubes, graphene or graphite or mixtures thereof.

Thanks to this solution, the first textile fibre based filament can be made electrically conductive in a safe, relatively simple may, to obtain a sensor with high biocompatibility for the plant and high electrical conductivity.

According to a further aspect of the invention, extremity portions of the first filament, placed outside the trunk of the plant, are each connected to a respective electrode, of which a first electrode is earthed and to a second electrode a negative potential is applied; and wherein to an extremity portion of the control electrode, placed outside the trunk of the plant, a positive potential is applied, so that the extremity portions of the first filament make up the "drain" and "source" of a transistor and the extremity portion of the control electrode makes up a "gate" of the transistor when the sap which flows along the conductor vessel puts the first filament and the control electrode in contact.

Thanks to this solution, the sensor has an organic electrochemical transistor (OECT) architecture, in which the active channel is defined by the conductor vessels of the plant in which the sap flows. In particular, this architecture makes it possible to have a sensor that has high amplification and high transconductance.

Alternatively, according to an aspect of the invention an extremity portion of the first filament, placed outside the trunk of the plant, can be connected to an electrode, and between the electrode and an extremity portion of the control electrode, placed outside the trunk of the plant, a potential difference can be applied, so that the extremity portions of the first filament and of the control electrode make up a potentiometric sensor when the sap which flows along the conductor vessel wets and or puts in (electrical) contact the first filament and the control electrode.

Thanks to this solution, the sensor has an architecture of a potentiometric sensor, which is simpler than the OECT sensor.

Advantageously, the textile fiber can be a natural textile fibre or, alternatively or additionally, the textile fiber can be a synthetic textile fiber.

Thanks to this solution, the textile fiber can have high biocompatibility for the plant.

According to an additional aspect of the invention, the control electrode can comprise or consist of a second electrically conductive filament, in which the second filament comprises a textile fiber coated with a layer of conductive polymer (for example of the type described above).

Thanks to this solution it is possible also to improve the biocompatibility of the control electrode and, hence, of the entire sensor.

According to a further aspect of the invention, the control electrode can comprise an at least partially metallic composition comprising at least one noble metal.

Thanks to this solution, it is possible to measure, by means of the sensor, the concentration of different substances present in the sap of the plant.

For example, the noble metal can be Silver (Ag) for the determination of the concentration of the positive ions present in the sap.

In this way, by means of the sensor it is possible to measure the concentration of the electrolytes present in the sap of the plant (Sodium, Calcium, Potassium and Magnesium) as a whole.

In this case, for example, the first filament comprises a selective membrane for determining the concentration of a specific positive ion among positive ions present in the sap.

Thanks to this solution, it is possible to selective measure the concentration of different positive ions, for example Sodium, Calcium, Potassium and Magnesium, one for each selective membrane.

Alternatively, the noble metal could be Platinum (Pt) for the determination of the concentration of molecules oxidised catalytically by the Platinum that are present in the sap, such as Glucose, Nitrates and others.

In this way, by means of the sensor it is possible to measure the concentration of the molecules oxidised catalytically by the Platinum which are present in the sap of the plant as a whole.

In this case, the first filament comprises a selective enzyme for determining the concentration of a specific molecule oxidized in a catalytic way by the Platinum present in the sap.

In this case, it is possible to have, from the sensor, a selective measure of the concentration of the given molecule to be monitored.

An additional aspect of the invention, for the same purposes described above, provides a system for determining biochemical parameters in the sap of a plant, which comprises:
   an electrochemical sensor as described above, and
   an electronic control unit operatively connected to the electrochemical sensor.

Advantageously, the system can comprise a hygrometer operatively connected to the electronic control unit and placed in the proximity of the plant.

Thanks to this solution it is possible to correlate the values measured by the sensors in terms of composition of the sap with the data of contribution of water (and nutrient substances) due to the (natural and/or artificial) of the plant itself.

Alternatively or additionally, the system can comprise a solar radiation intensity meter operatively connected to the electronic control unit and placed in the proximity of the plant.

Thanks to this solution it is possible to correlate the values measured by the sensors in terms of composition of the sap with the data of solar exposure of the plant itself.

In addition, the system could comprise a voltage generator, for example a battery which may be powered by a photovoltaic panel, which voltage generator is operatively connected to the electronic control unit and placed in the proximity of the plant.

Thanks to this solution, the sensor can be installed in the plant and be substantially autonomous from the energy viewpoint.

An additional aspect of the invention, for the same purposes described above, provides a method for measuring biochemical parameters in the sap of a plant, which comprises the steps of:
   inserting in a trunk of the plant a first electrically conductive filament comprising a textile fiber coated with a layer of conductive polymer, so that the first filament crosses a conductor vessel of the trunk of the plant wherein the sap flows;
   inserting in the trunk of the plant a control electrode, for example not in contact with the first filament, which crosses the conductor vessel;
   wetting by means of the sap of the plant the first filament and the control electrode;
   applying to the first filament and the control electrode at least a potential; and
   measuring at least a biochemical parameter of the sap of the plant according to a variation in the applied potential.

BRIEF DESCRIPTION OF THE DRAWINGS

Further features and advantages of the invention shall become readily apparent from reading the following description provided by way of non-limiting indication, with the aid of the figures illustrated in the accompanying drawings.

BEST EMBODIMENT OF THE INVENTION

With particular reference to the figures, the numeral 10 globally indicates an electrochemical sensor for measuring (on site) biochemical parameters in the sap L of a plant P.

The sap L could be crude or xylem sap or processed or phloem sap and it flows in channels defined by the conductor vessels C, i.e. respectively xylems and phloems, which develop along a trunk F of a plant, the term "trunk of the plant" meaning a trunk or a branch of the plant.

In particular, the sensor 10 is an integrated sensor in the plant P, or in the trunk D of the plant.

Figure 4:
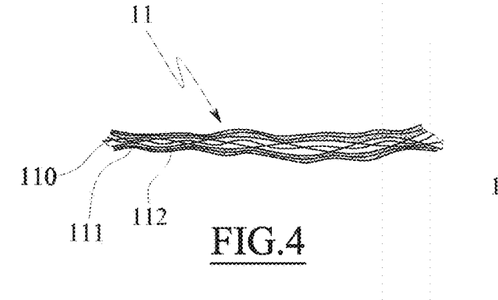
FIG. 4 is a schematic view of a first filament of a sensor according to the invention.

The sensor 10 comprises a first filament 11 comprising a textile fiber 110.

For example, the textile fiber 110 of which the first filament 11 is made is a natural textile fiber, for example selected in the group consisting of cotton, silk, wool and linen.

Alternatively, the textile fiber 110 of which the first filament 11 is made can be a synthetic textile fiber, for example selected in the group consisting of nylon or acrylic.

For example, the textile fiber 110 of which the first filament 11 is made is at least partially absorbent.

The first filament 11 comprises a first layer 111 which coats (totally or at least partially) the textile fiber 110 along its (entire) longitudinal extension.

The first layer 111 is made of a conductive polymer.

The conductive polymer is chosen in the group consisting of poly(3,4-ethylenedioxythiophene)-based polymer (PEDOT), poly(pyrroles) (PPY), polycarbazoles, polyindoles, polyazepines, polyanilines (PANI), polyacetylenes (PAC), poly(p-phenylene vinylene) (PPV)), polymers added with micro or nano conductive particles, such as silver or gold, carbon nanotubes, graphenes or graphites or mixtures of the same.

Advantageously, the conductive polymer is chosen in the group consisting of a doped compound belonging to the following class:

PEDOT:PSS (poly(3,4-ethylenedioxythiophene:polystyrene sulfonate) possibly doped with ethylene glycol and dodecylbenzenesulfonic acid (DBSA);

PEDOT:TOS poly(3,4-ethylenedioxythiophene:tyosilate); and

PEDOT:PPS poly(3,4-ethylenedioxythiophene:poly(p-phenylene sulfide.

Advantageously, the conductive polymer is PEDOT:PSS which is dissolved in aqueous solution (1% by weight), added with ethylene glycol (15% by volume) and dodecylbenzenesulfonic acid (DBSA) (1% by volume).

The coating of the first filament 11, or of the textile fiber 110, with the first layer 111 of conductive polymer can be obtained by immersing the textile fiber 110 in a solution of conductive polymer, as described above, and drying the conductive polymer on the textile fiber 110, for example for approximately 1 hour at 120-150° C.

The thickness of the first layer 111 of conductive polymer 110 is substantially between 50 and 200 nm.

The overall electric conductivity of the first filament 11, thus obtained, is between 80 and 400 Ohm/cm.

The length of the first filament 11 is determined according to the trunk D of the plant P.

For example, the length of the first filament 11 is greater than the maximum diameter of the trunk D of the plant P in the cross section thereof, in which the first filament is to be installed.

The first filament 11 can comprise a second layer 112 which coats (totally or at least partially) the textile fiber 110, i.e. the first layer 111, along its (entire) longitudinal extension.

The second layer 112 is obtained from (or comprises) a selective compound. The selective compound is chosen in the group consisting of a selective enzyme and of a selective membrane.

For example, the selective compound and, hence, the selective enzyme and the selective membrane are chosen according to the type of analyte present in the sap L to be analysed and to be measured by means of the sensor 10. For example, the selective enzyme, chosen according to the analyte to be determined, is chosen in the group consisting of:

glucose oxidase (GOx), for determining glucose in the sap L;

lactate oxidase (LOx), for determining lactic acid in the sap L;

Nitrogenase, for determining nitrate in the sap L;

urease for determining urea in the sap L.

The second layer 112 containing the selective enzyme can be obtained according to one of the following methods:

i) immersing the first filament 11, or the textile fiber 110 coated with the first layer 111, into a solution of the enzyme and subsequently drying at ambient temperature for approximately 2 hours, or ii) immersing the first filament 11, or the textile fiber 110 coated with the first layer 111, into a solution of enzyme and chitosan for approximately 5 hours and subsequent drying at ambient temperature, or iii) immersing the first filament 11, or the textile fiber 110 coated with the first layer 111, first in a chitosan solution as defined below and then an enzyme solution as defined below, followed by drying at ambient temperature, or iv) immersing the first filament 11, or the textile fiber 110 coated with the first layer 111, in a solution of poly(glycidyl methacrylate) (PGMA) and poly(2-hydroxyethyl methacrylate) (PHEMA) mixed with enzyme.

The chitosan solution has a concentration of approximately 5 mg/ml and it can be prepared for example by dissolving chitosan (0.5 g) in an aqueous solution of acetic acid (100 ml, 5 mM, pH=5-6). To 50 µL of chitosan solution are added 5 µL of an enzyme solution (concentration 8 mg/ml) and the resulting solution is buffered with PBS solution (Phosphate Buffered Saline, pH=7.2).

For example, the (ion)selective membrane, chosen as a function of the analyte to be determined, can be a membrane for determining potassium.

For example, the (ion)selective membrane is chosen among a first membrane having the following composition: a mixture of tetrahydrofuran (THF) with polyvinyl chloride (PVC) with high molecular weight (HW), for example 30-37% by weight; diisodecyl adipate (DOA), for example between 60 and 66% by weight; potassium tetrakis(4-chlorophenyl)borate (KTpClPB), for example 0.5% by weight; and potassium ionophore III, for example between 1 and 2.5% by weight, and a second membrane for the sodium ion having the following composition: tetrahydrofuran THF=1.5 mL; sodium ionophore (0.70% by weight):potassium tetrakis borate (0.20% by weight) 2-nitrophenyl octyl ether (66.1% by weight) PVC (33% by weight).

For example, the second layer 112 containing the (ion) selective membrane can be obtained by immersing the first filament 11, or the textile fiber 110 coated with the first layer 111, in a solution containing:

a mixture of tetrahydrofuran (THF) with polyvinyl chloride (PVC) with high molecular weight (HW), for example 30-37% by weight; diisodecyl adipate (DOA), for example between 60 and 66% by weight; potassium tetrakis(4-chlorophenyl)borate (KTpClPB), for example 0.5% by weight; and potassium ionophore III, for example between 1 and 2.5% by weight.

Figure 5:
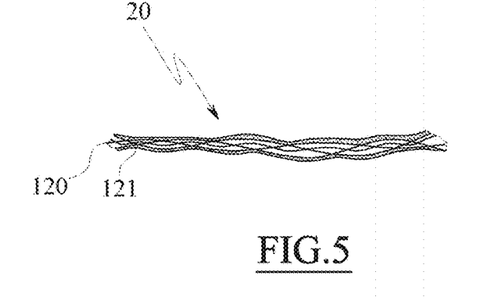
FIG. 5 is a schematic view of a control electrode according to an embodiment of a sensor according to the invention.

The sensor 10 comprises a control electrode 12.

The control electrode 12 is for example wire-like (and flexible).

The control electrode 12 can be defined by a metal wire, for example a noble metal, for example Silver (Ag) or Platinum (Pt).

Alternatively, the control electrode 12 can be defined by a second filament comprising a second textile fiber 120.

For example, the second textile fiber 120 of which the first filament 11 is made is a natural textile fiber, for example selected in the group consisting of cotton, silk, wool and linen.

Alternatively, the second textile fiber 110 of which the second filament is made can be a synthetic textile fiber, for example selected in the group consisting of nylon or acrylic.

For example, the second textile fiber 120 of which the second filament is made is at least partially absorbent.

The second filament that defines the control electrode 12 comprises a layer 121 which coats (totally or at least partially) the second textile fiber 120 along its (entire) longitudinal extension.

The layer 121 is made of a conductive polymer.

The conductive polymer is chosen in the group consisting of poly-oligo-thiophenes such as poly(3,4-ethylenedioxythiophenes) (PEDOT); poly(pyrroles) (PPY), polycarbazoles, polyindoles, polyazepines, polyanilines (PANI), polyacetylenes (PAC), poly(p-phenylene vinylene) (PPV)), polymers added with micro or nano conductive particles, such as silver or gold, carbon nanotubes, graphenes or graphites or mixtures of the same.

Advantageously, the conductive polymer is chosen in the group consisting of a doped compound belonging to the following class:

PEDOT:PSS (poly(3,4-ethylenedioxythiophene:polystyrene sulfonate) possibly doped with ethylene glycol and dodecylbenzenesulfonic acid (DBSA);

PEDOT:TOS poly(3,4-ethylenedioxythiophene:tyosilate); and

PEDOT:PPS poly(3,4-ethylenedioxythiophene:poly(p-phenylene sulfide.

Advantageously, the conductive polymer is PEDOT:PSS which is dissolved in aqueous solution (1% by weight), added with ethylene glycol (15% by volume) and dodecylbenzenesulfonic acid (DBSA) (1% by volume).

The coating of the second filament 12 which defines the control electrode 12, or of the second textile fiber 120, with the layer 121 of conductive polymer can be obtained by immersing the second textile fiber 120 in a solution of conductive polymer, as described above, and drying the conductive polymer on the second textile fiber 120, for example for approximately 1 hour at 120-150° C.

The thickness of the layer 121 of conductive polymer that coats the second fiber 120 is substantially between 50 and 200 nm.

The overall electric conductivity of the second filament that defines the control electrode 12 thus obtained is between 80 and 400 Ohm/cm.

The second filament that defines the control electrode 12 can comprise (or consist of) a noble metal, for example Silver (Ag), Platinum (Pt) or Copper (Cu), for example it can be at least partially coated thereby or have particles of said noble metal finely dispersed in the layer 121.

The length of the control electrode 12 is determined according to the trunk D of the plant P.

For example, the length of the control element 12 is greater than the maximum diameter of the trunk D of the plant P in the cross section thereof, in which the control electrode is to be installed.

Thus, the sensor 10 comprises a first filament 11, a second filament 12 and at least one conductor vessel C, preferably a plurality of conductor vessels C of a trunk D of a plant, configured as described below.

Figure 3:
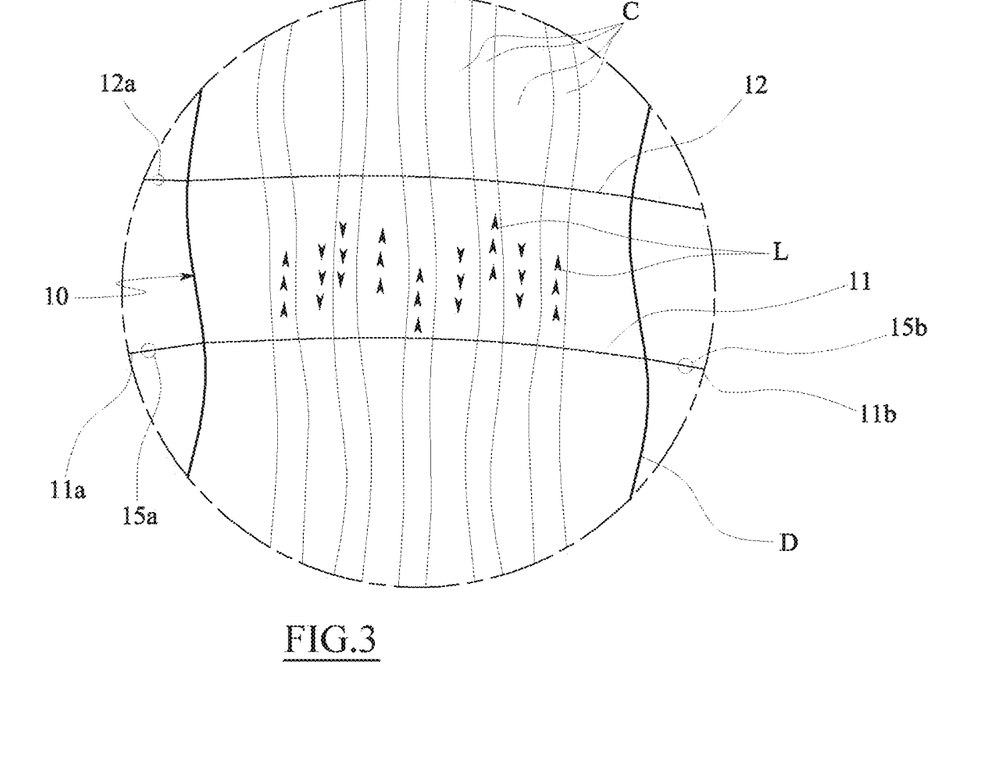
FIG. 3 is an enlargement of FIG. 1 and FIG. 2.

In practice, the first filament 11 crosses the trunk D of the plant, for example in transverse direction with respect to the direction of flow of the sap L along the conductor vessels C, for example along a diameter of the trunk D of the plant P.

In practice the first filament 11 is able to cross one or more conductor vessels C so as to be wet by the sap L.

For example, the first filament 11 is placed in the trunk D of the plant P so that its free extremities 11a,11b project outside the trunk D itself.

In this way, the central portion of the first filament 11, which is placed inside the trunk D of the plant P, crosses transversely the conductor vessels C and is wet by the sap L, which is at least partially absorbed by the first filament 11, or by the textile fiber 11 thereof.

The control electrode 12 also crosses the trunk D of the plant P, for example in transverse direction with respect to the direction of flow of the sap L along the conductor vessels C, for example along a diameter of the trunk D of the plant P (and is substantially parallel to the first filament 11).

In practice, the control electrode 12 is able to cross one or more conductor vessels C so as to be wet by the sap L.

In this way, the central portion of the control electrode 12, which is placed inside the trunk D of the plant P, crosses transversely the conductor vessels C and is wet by the sap F of the plant P.

The control electrode 12 is placed upstream or downstream relative to the first filament 11 in the direction of flow of the sap L along the conductor vessels C.

The control electrode 12 and the first filament 11 are not in mutual contact.

For example, the control electrode 12 and the first filament 11 are placed at a substantially non-zero mutual distance, for example between 10 μm and 5 cm, for example between 0.5 cm and 1 cm.

For example, the control electrode 12 is placed in the trunk D of the plant P so that its free extremities 12a project outside the trunk D itself.

Figure 1:
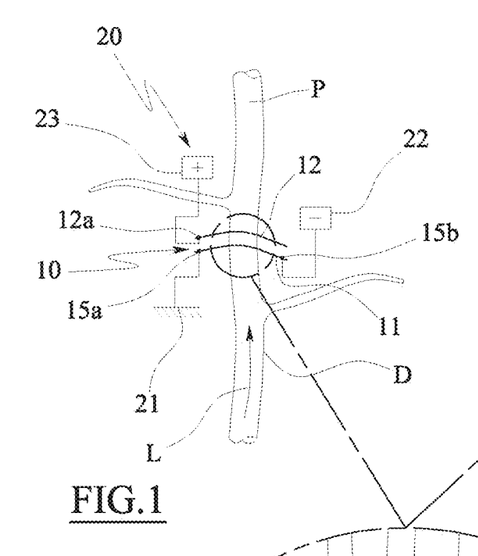
FIG. 1 is a schematic view of a first embodiment of a sensor for measuring biochemical parameters in the sap of a plant.

A first embodiment of the sensor 10, shown in FIG. 1, illustrates a first architecture in which the sensor 10 is used as an organic electrochemical transistor (OECT) sensor.

In the first embodiment, the extremities 11a,11b, or extremity portions of the first filament 11, which project outside the trunk D of the plant P, are each connected to a respective electrode 15a,15b (for example an electrical contact fixed to the first filament 11), of which:

a first electrode 15a is earthed ($V_0$) and to a second electrode 15b a negative potential ($V_-$), preferably from −0.1 Volts to −0.01 Volts (for example substantially equal to −0.1 Volts) is applied. To an extremity 12a of the control electrode 12, for example an extremity portion of the control electrode 12 that projects outside the trunk D of the plant P, a positive potential ($V_+$), for example substantially between 0.2 and 1 Volt is applied.

In this way, the axial portion of the conductor vessels C of the plant P crossed by the first filament 11 and by the control electrode 12 serves as a containment channel (tank) of an electrolyte consisting of the sap F of the plant P that flows in said conductor vessels C.

In practice, the extremities 11a,11b of the first filament 11, or the electrodes 15a,15b, respectively make up the "drain" and the "source" of a transistor and the extremity 12a of the control electrode 12 makes up a "gate" of the transistor when the sap L, which flows along the conductor vessels C crossed by the first filament 11 and by the control electrode 12, puts in electrical contact the first filament 11 and the control electrode 12.

The sensor 10, in this first embodiment, is connected to a first measuring circuit 20.

The first measuring circuit 20 comprises an earthing 21 connected, via the first electrode 15a, to the first extremity 11a of the first filament 11.

The first measuring circuit 20 comprises a first voltage generator 22, able to generate a negative voltage at the second extremity 15b of the first filament 11, or on the second electrode 15b connected thereto.

The first measuring circuit 20 comprises a second voltage generator 23, able to generate a positive voltage at one extremity 12a of the control electrode 12.

The first measuring circuit 20 can comprise a first ammeter configured to measure the current intensity $I_{drain/source}$ in the first filament 11.

The first and the second voltage generator can be defined by a (single) battery, for example a Lithium battery.

For example, the first and the second voltage generator can be powered electrically by a source of electricity, for example renewable, for example by a photovoltaic panel 25.

The photovoltaic panel 25 is for example placed in the proximity of the plant P, for example in the same soil where the plant is rooted or in an adjoining area.

The first measuring circuit 20 comprises a second ammeter configured to measure the current intensity $I_{gate}$ in the circuit connected to the control electrode 12.

Figure 6:
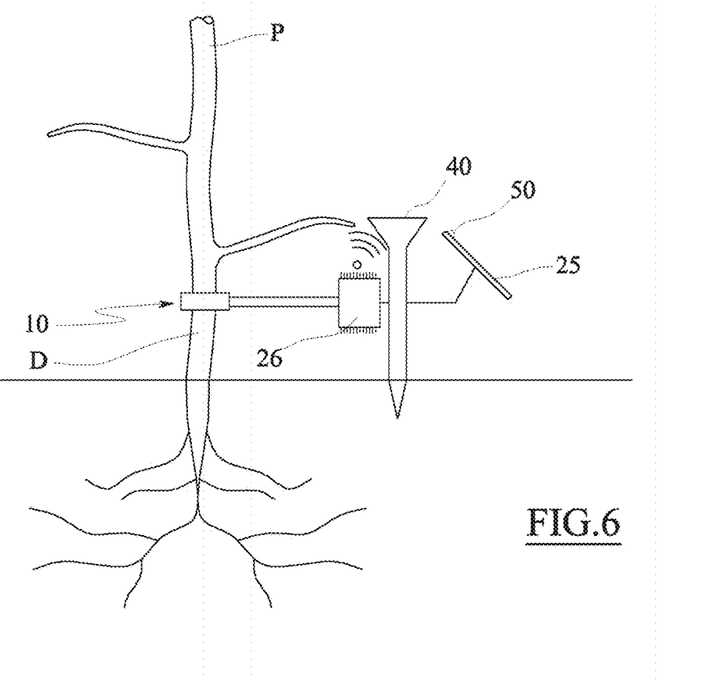
FIG. 6 is a schematic view of a system for determining a biochemical parameter in the sap of a plant provided with a sensor according to the invention.

The measuring circuit 20 comprises an electronic control unit 26 operatively connected to the first filament 11, via the electrodes 15a,15b, to the control electrode 12, via its extremity 12a, to the first and to the second voltage generator (the battery) and to the first and to the second ammeter.

The electronic control unit 26 comprises a memory.

The electronic control unit 26 comprises a data transmission unit, for example of the wireless type (exploiting radio and/or telephone transmission) The first and the second ammeter (and/or the first and second voltage generator) for example can be integrated in the electronic control unit 26. Moreover, the electronic control unit 26 can be operatively connected to a hygrometer 40, which is for example placed in the proximity of the plant P, for example in the same soil where the plant is rooted or in an adjoining area.

In addition, to the electronic control unit 26 can be operatively connected a solar radiation intensity meter 50, which is for example placed in the proximity of the plant P, for example in the same soil in which the plant is rooted or in an adjoining area, for example the solar radiation intensity meter 50 can be integrated on the photovoltaic panel 25.

In practice, the operation of the sensor 10 in this first embodiment is as follows.

Between source and drain (i.e. between the extremities 11a,11b of the first filament 11) a constant potential difference $(V--V_0)$ is applied that generates a current $I_{drain/source}$ (whose value is predefined) that flows in the first filament 11. Between the first filament 11 and the control electrode 12 a positive potential difference is applied and, hence, the positive ions present in the sap F that connects them electrically (and wets them) are directed from the control electrode 12 (gate) towards the first filament 11 (source-drain).

The current $I_{drain/source}$ generated on the first filament 11 is modified (with respect to the predefined value) proportionately to the concentration of positive ions contained in the sap F.

The electronic control unit 26 is configured to calculate the concentration of the free positive ions in the sap L of the plant P, as a function of the measurement of the variation of the modulation of the current $I_{drain/source}$ (measured by means of the first ammeter), caused by the gate potential.

Figure 2:
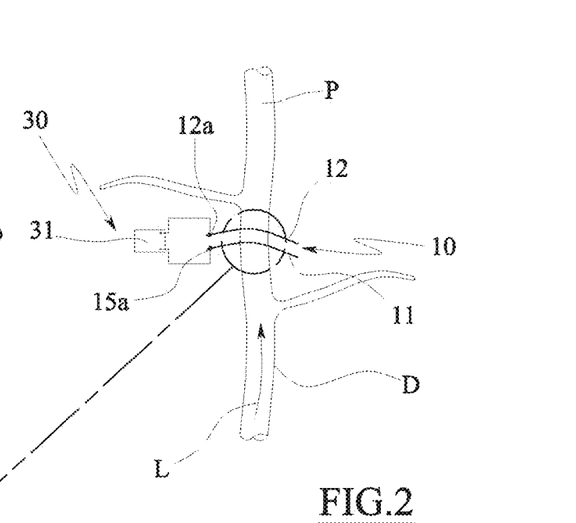
FIG. 2 is a schematic view of a second embodiment of a sensor for measuring biochemical parameters in the sap of a plant.

A second embodiment of the sensor 10, shown in FIG. 2, illustrates a second architecture in which the sensor 10 is used as a potentiometric sensor.

In the second embodiment, a (single) extremity 11a,11b, of the first filament 11 (or an extremity portion of the first filament 11 that projects outside the trunk D of the plant P) is connected to a (single) electrode 15a,15b, for example an electrical contact fixed to the first filament 11.

Between the electrode 15a and an extremity 12a of the control electrode 12 (or an extremity portion of the control electrode 12 that projects outside the trunk D of the plant P) a (pre-set) potential difference ($\Delta V$) is applied, for example substantially between 0.2 and 1 Volt, for example equal to 0.6 Volts. In this way, the extremity 11a (or the electrode 15a) of the first filament 11 and the end 12a of the control electrode 12 make up a potentiometric sensor when the sap L that flows along the conductor vessels C crossed by the first filament 11 and by the control electrode 12 wets (and puts in electrical contact) the first filament 11 and the control electrode 12.

The sensor 10, in this second embodiment, is connected to a second measuring circuit 30.

The second measuring circuit 30 comprises a voltage generator 31, able to generate a voltage difference between the first end 15a of the first filament 11, or between the first electrode 15a connected thereto, and the extremity 12a of the control electrode 12.

The voltage generator 31 can be defined by a battery, for example a Lithium battery.

For example, the voltage generator 31 can be powered electrically by a source of electricity, for example renewable, for example by a photovoltaic panel 25.

The photovoltaic panel 25 is for example placed in the proximity of the plant P, for example in the same soil where the plant is rooted or in an adjoining area.

The second measuring circuit 30 can comprise a voltmeter configured to measure the variation of the potential difference between the first filament 11 and the control electrode 12.

The second measuring circuit 30 comprises an electronic control unit 26 operatively connected to the first filament 11, via the electrode 15a, to the control electrode 12, via its extremity 12a, to the voltage generator (the battery) and to the voltmeter.

The electronic control unit 26 comprises a memory.

The electronic control unit 26 comprises a data transmission unit, for example of the wireless type (exploiting radio and/or telephone transmission) The voltmeter (as well as the voltage generator 31) can be integrated in the electronic control unit 26.

Moreover, the electronic control unit 26 can be operatively connected to a hygrometer 40, which is for example placed in the proximity of the plant P, for example in the same soil where the plant is rooted or in an adjoining area.

In addition, to the electronic control unit 26 can be operatively connected a solar radiation intensity meter 50, which is for example placed in the proximity of the plant P, for example in the same soil in which the plant is rooted or in an adjoining area, for example the solar radiation intensity meter 50 can be integrated on the photovoltaic panel 25.

In practice, the operation of the sensor 10 in this second embodiment is as follows.

Between the first filament 11 and the control electrode 12 a potential difference $\Delta V$ is applied, which generates a current when the first filament 11 and the control electrode 12 are wet by the same sap L, or are in electrical contact through the sap F that flows along the conductor vessels C.

The electronic control unit 26 is configured to measure the variation of the potential difference ΔV and to determine the concentration of the free positive ions in the sap L of the plant P, as a function of the measurement of the variation of the potential difference ΔV (measured by means of the voltmeter).

Moreover, if the control electrode 12 is made of or comprises Silver (Ag), then it is possible to measure the concentration of free positive ions, such as Sodium ($Na^+$), Potassium ($K^+$), Calcium ($Ca^{++}$) and Magnesium ($Mg^{++}$), present in the sap L.

If it is necessary to measure the concentration of only one of these free positive ions in the sap L, it is possible to use as the first filament 11 of the sensor 10, a first filament 11 provided with a selective membrane.

For example, to measure the concentration of Potassium ($K^+$) it is possible to use a selective membrane, like the one described above, in the first filament 11.

Moreover, if the control electrode 12 is made of or comprises Platinum (Pt), then it is possible to measure the concentration of the free molecules that are oxidised catalytically by Platinum which are present in the sap L, such as Glucose, Lactic Acid, Nitrates and Urea.

If it is necessary to measure the concentration of only one of these free molecules in the sap L, it is possible to use as the first filament 11 of the sensor 10, a first filament 11 provided with a selective enzyme, as described above.

In practice, in these cases the selective enzyme used in the first filament 11 promotes a well known reaction only with the corresponding free molecule, allowing the production of $H^+$ ions in a proportional quantity to the concentration of molecule present in the sap F. The concentration of the molecule is proportional to the variation of the current intensity $I_{drain/source}$ or to the variation of potential difference between first filament 11 and the control electrode 12 and, hence, it can be determined on the basis of the measurement thereof, according to the methods exposed above.

Furthermore (in both embodiments described above) it is possible to provide a plurality of sensors 10 (equal to each other or different) integrated as described above in the same plant P, for example operatively connected to the same electronic control unit 26 or to a plurality thereof.

It is also possible to provide a plurality of sensors 10 integrated as described above in different plants P, for example operatively connected to the same electronic control unit 26 or to a plurality thereof.

Figure 7:
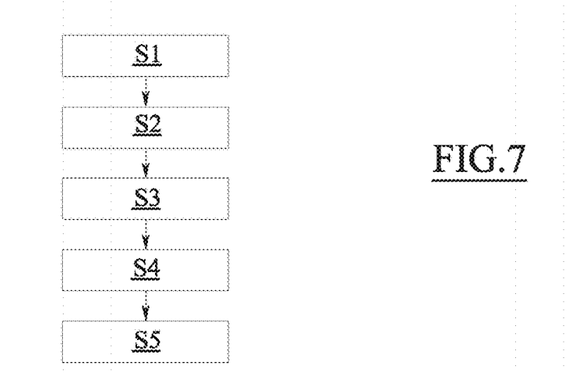
FIG. 7 is a schematic view of a flowchart of a method for determining a biochemical parameter in the sap of a plant by means of a sensor according to the invention.

In light of the above description, the method for measuring biochemical parameters in the sap L of a plant P comprises the following steps shown schematically in FIG. 7.

First of all the method comprises integrating the sensor 10 in the trunk D of the plant P.

In practice, the method comprises inserting (block S1) in the trunk D of the plant P, for example in a first predetermined insertion point, a first filament as described above (depending on requirements).

The insertion of the first filament 11 is carried out so that the first filament 11 crosses one or a plurality of conductor vessels C of the trunk D of the plant P in which the sap L flows, in which the direction of crossing of the first filament 11 is transverse (e.g. orthogonal) relative to the flowing direction of the sap L along the conductor vessels C.

In practice, the first filament 11 is positioned so that at least one or both its extremities 11a, 11b project outside the trunk D of the plant P, for example from (diametrically) opposite parts thereof.

The method further comprises inserting (block S2) in the trunk D of the plant P a control electrode 12, as described above (depending on requirements), which crosses the conductor vessels C, for examples substantially the same conductor vessels C intercepted by the first filament 11, although not necessarily the same.

The insertion of the control element 12 is carried out so that the control electrode 12 crosses one or a plurality of conductor vessels C of the trunk D of the plant P in which the sap L flows, in which the direction of crossing of the control electrode 12 is transverse (e.g. orthogonal) relative to the flowing direction of the sap L along the conductor vessels C.

In practice, the control element 12 is positioned so that at least one or both its extremities 12a project outside the trunk D of the plant P, for example from (diametrically) opposite parts thereof.

For example, the control electrode 12 is inserted in a predetermined second insertion point axially separated from the first insertion point and, preferably, positioned downstream relative thereto in the flowing direction of the sap L along the conductor vessel C. In practice, the control electrode 12 is more distal from the root area of the plant P relative to the first filament 11.

The method, moreover, comprises letting the sap L that flows in the conductor vessels C intercepted by the first filament 11 and by the control electrode 12 to wet them, in practice the sap wets (block S3) (and electrically connects) the first filament 11 and the control electrode 12.

The method then comprises applying (block S4) to the first filament 11 and the control electrode 12 at least an electrical potential.

For example, the step of applying the potential can be carried out according to the first architecture, described above in the first embodiment of the sensor 10 and shown in FIG. 1, or according to the second architecture, described above in the second embodiment of the sensor 10 and shown in FIG. 2.

The method then comprises measuring (block S5), as described above, at least one biochemical parameter, for example the concentration of one or more free positive ions and/or the concentration of one or more molecules oxidised catalytically by Platinum, of the sap L of the plant P as a function of a variation of the applied potential.

For example, through the measurement, repeated over time (for example during the 24 hours of the day and on multiple days) it is possible to continuously monitor (in real time) and on site the daily and/or seasonal changes of the measured biochemical parameters, correlating these repeated measures, moreover, with the hygrometric and solar radiation data measured, respectively, by the hygrometer 40 and by the solar radiation intensity meter 50.

The invention thus conceived is susceptible to many modifications and variants, all falling within the same inventive concept.

Furthermore, all details may be replaced by technically equivalent elements. In practice, the materials used, as well as their shapes and dimensions, can be of any type according to the technical requirements without thereby departing from the scope of protection of the following claims.

The invention claimed is:

1. An electrochemical sensor for measuring biochemical parameters in the sap of a plant, comprising:

a channel in which the sap of a plant flows;
a first electrically conductive filament which crosses the channel;
a control electrode which crosses the channel;
wherein the channel comprises a conductor vessel of a trunk of the plant,
wherein the first filament comprises a textile fiber coated with a layer of conductive polymer, and
wherein extremity portions of the first filament, placed outside the trunk of the plant, are each connected to a respective electrode, of which a first electrode is earthed and to a second electrode a negative potential is applied, and wherein to an extremity portion of the control electrode, placed outside the trunk of the plant, a positive potential is applied, so that the extremity portions of the first filament make up the "drain" and "source" of a transistor and the extremity portion of the control electrode makes up a "gate" of the transistor when the sap which flows along the conductor vessel puts the first filament and the control electrode in contact.

2. The sensor according to claim 1, wherein the conductive polymer making up the layer is chosen in the group among a poly(3,4-ethylenedioxythiophene)-based polymer (PEDOT), poly(pyrroles) (PPY), polycarbazoles, polyindoles, polyazepines, polyanilines (PANI), polyacetylenes (PAC), poly(p-phenylene vinylene) (PPV)), polymers added with micro or nano conductive particles of silver or gold, carbon nanotubes, graphenes or graphites or mixtures of the same.

3. The sensor according to claim 1, wherein the textile fiber is a natural textile fiber.

4. The sensor according to claim 1, wherein the textile fiber is a synthetic textile fiber.

5. The sensor according to claim 1, wherein the conductor vessel is chosen in the group made up of xylem and phloem.

6. The sensor according to claim 1, wherein the control electrode comprises a second electrically conductive filament, in which the second filament comprises a textile fiber coated with a layer of conductive polymer.

7. The sensor according to claim 1, wherein the control electrode comprises an at least partially metallic composition comprising at least a noble metal.

8. The sensor according to claim 7, wherein the noble metal is Silver (Ag) for determining the concentration of the positive ions present in the sap.

9. The sensor according to claim 7, wherein the first filament comprises a selective membrane for determining the concentration of a specific positive ion among positive ions present in the sap.

10. The sensor according to claim 7, wherein the noble metal is Platinum (Pt) for determining the concentration of molecules oxidized in a catalytic way by the Platinum present in the sap.

11. The sensor according to claim 7, wherein the first filament comprises a selective enzyme for determining the concentration of a specific molecule oxidized in a catalytic way by the Platinum present in the sap.

12. A system for determining biochemical parameters in the sap of a plant which comprises:
an electrochemical sensor according to claim 1,
an electronic control unit operatively connected to the electrochemical sensor.

13. The system according to claim 12, which comprises a hygrometer operatively connected to the electronic control unit and placed in the proximity of the plant.

14. The system according to claim 12, which comprises a solar radiation intensity meter operatively connected to the electronic control unit and placed in the proximity of the plant.

15. The system according to claim 12, which comprises a power voltage generator operatively connected to the electronic control unit and placed in the proximity of the plant.

16. A method for measuring biochemical parameters in the sap of a plant which comprises the steps of:
inserting in a trunk of the plant a first electrically conductive filament comprising a textile fiber coated with a layer of conductive polymer, so that the first filament crosses a conductor vessel of the trunk of the plant wherein the sap flows;
inserting in the trunk of the plant a control electrode which crosses the conductor vessel;
wetting by means of the sap of the plant the first filament and the control electrode;
applying at least a potential to the first filament and the control electrode, wherein extremity portions of the first filament, placed outside the trunk of the plant, are each connected to a respective electrode, of which a first electrode is earthed and to a second electrode a negative potential is applied, and wherein to an extremity portion of the control electrode, placed outside the trunk of the plant, a positive potential is applied, so that the extremity portions of the first filament make up the "drain" and "source" of a transistor and the extremity portion of the control electrode makes up a "gate" of the transistor when the sap which flows along the conductor vessel puts the first filament and the control electrode in contact; and
measuring at least a biochemical parameter of the sap of the plant according to a variation in the applied negative potential and positive potential.

17. An electrochemical sensor for measuring biochemical parameters in the sap of a plant, comprising:
a channel in which the sap of a plant flows;
a first electrically conductive filament which crosses the channel;
a control electrode which crosses the channel;
wherein the channel comprises a conductor vessel of a trunk of the plant,
wherein the first filament comprises a textile fiber coated with a layer of conductive polymer, and
wherein the control electrode comprises a second electrically conductive filament, in which the second filament comprises a textile fiber coated with a layer of conductive polymer, or wherein the control electrode comprises an at least partially metallic composition comprising at least a noble metal.

* * * * *